United States Patent [19]

Takasugi

[11] Patent Number: 4,735,211

[45] Date of Patent: Apr. 5, 1988

[54] ULTRASONIC MEASUREMENT APPARATUS

[75] Inventor: Wasao Takasugi, Higashiyamato, Japan

[73] Assignee: Hitachi, Ltd., Tokyo, Japan

[21] Appl. No.: 824,734

[22] Filed: Jan. 31, 1986

[30] Foreign Application Priority Data

Feb. 1, 1985 [JP] Japan .................................. 60-16528

[51] Int. Cl.$^4$ ................................................ A61B 10/00
[52] U.S. Cl. ..................................... 128/660; 128/663
[58] Field of Search ........................... 128/660–663; 73/618–620

[56] References Cited

U.S. PATENT DOCUMENTS

| | | | |
|---|---|---|---|
| 4,037,585 | 7/1977 | Gildenberg | 128/653 X |
| 4,059,098 | 11/1977 | Murdock | 128/660 |
| 4,111,055 | 9/1978 | Skidmore, III | 128/661 X |
| 4,463,763 | 8/1984 | Koyano et al. | 128/661 |
| 4,547,892 | 10/1985 | Richey et al. | 128/661 X |
| 4,566,459 | 1/1986 | Umemura et al. | 128/660 |
| 4,593,314 | 6/1986 | Siler | 128/660 |
| 4,630,612 | 12/1986 | Uchida et al. | 128/660 |

Primary Examiner—Francis J. Jaworski
Attorney, Agent, or Firm—Antonelli, Terry & Wands

[57] ABSTRACT

An ultrasonic measurement apparatus provided with a probe connected to a Doppler flow meter, and a movement detecting probe, both of which probes are mounted on an actuator, which is driven by a synthesizer which is adapted to repeatedly reproduce a set waveform synchronously with the cardiac motion of a living body, whereby the distance between the probes and a region of interest in the interior of the living body is kept substantially constant irrespective of the movement, which occurs due to the cardiac motion, of the region of interest to enable a measurement signal from the region of interest to be constantly obtained. The movement detecting probe is connected to a M-mode imaging apparatus to thereby make it possible that a M-mode image thereon be monitored to determine whether a suitable waveform is generated by the synthesizer.

5 Claims, 3 Drawing Sheets

ULTRASONIC MEASUREMENT APPARATUS

BACKGROUND OF THE INVENTION

This invention relates to a system for applying an ultrasonic probe to the surface of a living body to measure the reflected ultrasonic waves therefrom and thereby obtain an ultrasonic tomographic image, or determine a velocity of flow of the blood, and more particularly to a measurement apparatus using a measurement signal from a portion, which moves periodically due to the cardiac motion, of a living body.

In a diagnosis apparatus, it is greatly necessary to obtain information from a moving region of interest. Regarding, for example the heart, various diagnosis information of a high accuracy cannot be obtained without taking the influence of the cardiac motion into consideration. In order to meet these requirements, a measurement method utilizing an electrocardiogram as a synchronizing signal, i.e. the periodicity of a cardiac motion is widely used.

For example, the thesis entitled "Gated Cardiac Computed Tomography with a Motion Phantom" in the "Radiograph", Vol. 134, pp 213–217, points out that a clear stop motion cardiac image can be obtained by repeatedly collecting the special-phase data alone in a cardiac cycle in the X-ray computed tomography, and thereby reconstructing the image.

In the ultrasonic radiography, the real time imaging is required, and repeatedly collecting special-phase data in a cardiac cycle so as to obtain one picture is contradictory to this purpose. In an apparatus for measuring a flow rate of the blood in the heart or a blood vessel in the vicinity of the heart, the moving speed of the heart or blood vessel is superposed on the flow rate of the blood, and an object to be measured goes out of the visual field of measurement due to the cardiac motion in some cases.

SUMMARY OF THE INVENTION

According to the present invention, the ultrasonic measurement of a region of interest is conducted by moving an ultrasonic probe in accordance with a periodic movement of the region of interest to be measured, to maintain the variations in the relative distance between the probe and the region of interest substantially within a predetermined range of levels.

An object of the present invention is to provide an ultrasonic measurement apparatus which is capable of carrying out an ultrasonic measurement accurately at all times irrespective of the movement, which occurs due to the cardiac motion, of a region of interest.

Another object of the present invention is to provide an ultrasonic measurement apparatus which is adapted to obtain a real time high definition tomographic image of a predetermined portion, which is moved periodically in accordance with the cardiac motion, of a living body.

A characteristic structure according to the present invention includes a first ultrasonic probe adapted to transmit and receive by a main measuring instrument an ultrasonic wave to and from a living body, a second ultrasonic probe provided in the vicinity of the first probe and adapted to detect the movement of a region of interest in the interior of the living body, a M-mode imaging means adapted to apply a transmitting wave signal repeatedly to the second ultrasonic probe, and display a reception signal from the second ultrasonic probe on a two-dimensional image, one axis of which is a distance between the second ultrasonic probe and the region of the interest and the other axis of which is the lapse of time of repetition, a means for detecting the cardiac motion in the living body and generating a pulse signal which is synchronous therewith, a signal synthesizer adapted to reproduce a set waveform synchronously with the pulse signal, and an actuator adapted to be operated by an output from the synthesizer and periodically drive the first and second ultrasonic probes. According to this arrangement, the waveform set in the synthesizer is monitored with reference to the picture frame on the M-mode image taking means to determine whether the waveform is in conformity with the movement of the region of interest due to the cardiac motion, and a waveform of the movement agreeing therewith can be set. If a two-dimensional input tablet is provided on the picture frame on the M-mode image taking means so as to set in the synthesizer by this input tablet a waveform of the movement, which is due to the cardiac motion, of the region of interest, a suitable waveform-setting operation can be carried out easily.

The above-mentioned main measuring instrument consists typically of a pulse Doppler flow meter, which is adapted to set the distance between the first probe and the region of interest, and convert the quantity of Doppler shift of a reflection signal from the region of interest into a speed. Another example of a device used as the main measuring instrument is an ultrasonic tomographic image taking means which is capable of obtaining high density real time images from a moving target by an operation of the above-mentioned actuator.

DESCRIPTION OF THE PREFERRED EMBODIMENTS

Figure 1:
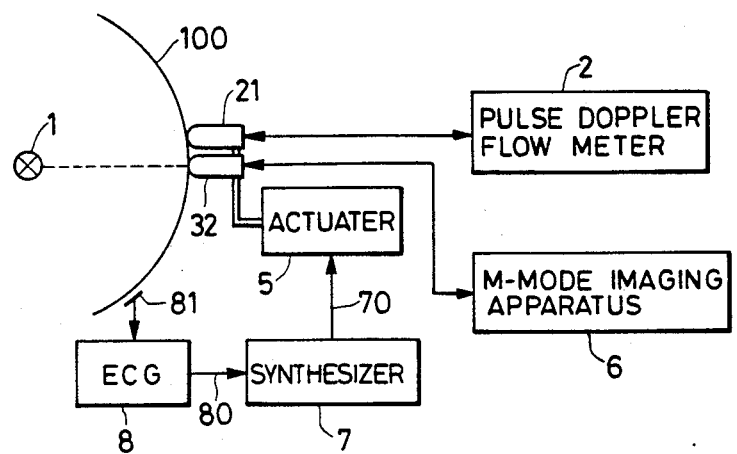
FIG. 1 is a block diagram of an embodiment of the present invention.

FIG. 1 shows the construction of an embodiment of the present invention. In this embodiment a pulse Doppler flow meter 2 is used as a main measuring instrument. An ultrasonic probe 21 connected to the pulse Doppler flow meter 2, and a movement-detecting ultrasonic probe 32 are mounted on an actuator 5. The actuator 5 is driven by an output 70 from a synthesizer to thereby cause the probes 21, 32 to be moved forward and backward synchronously with the cardiac motion of a region of interest 1 (a blood vessel near the heart in this embodiment) in the interior of a living body 100. An electrocardiograph detector 8 is adapted to detect an electrocardiograph signal of the living body by an electrode 81, and generate an output pulse 80 which is synchronous with the cardiac motion of the living body. The synthesizer 7 is also adapted to repeatedly reproduce the preset waveform in the output 70 synchronously with the output pulse 80. The ultrasonic probe 32 is connected to a M-mode imaging apparatus 6. The distance between the region of interest 1 and probe 32 can be monitored on the picture frame on the M-mode imaging apparatus 6 to determine whether the distance is constant irrespective of the cardiac motion, i.e., the waveform generated by the synthesizer 7 can be monitored on the sample picture frame to determine whether the waveform is suitable.

Figure 2:
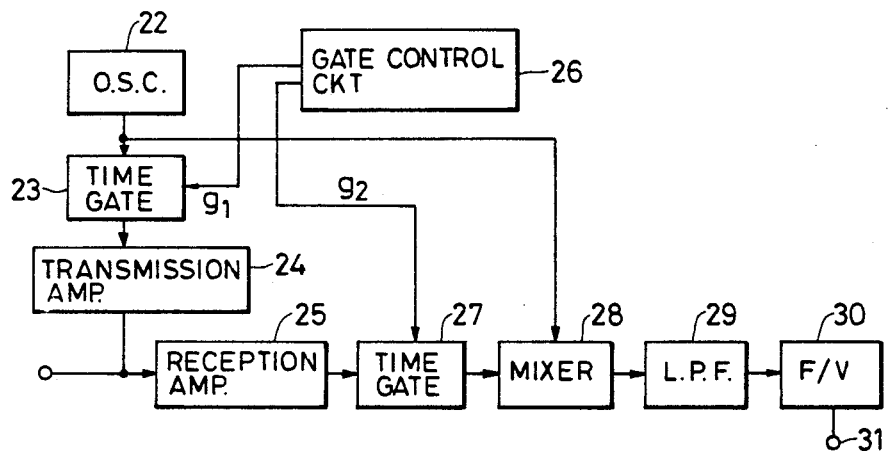
FIG. 2 is a block diagram of the details of the block 2 in FIG. 1.
Figure 3:
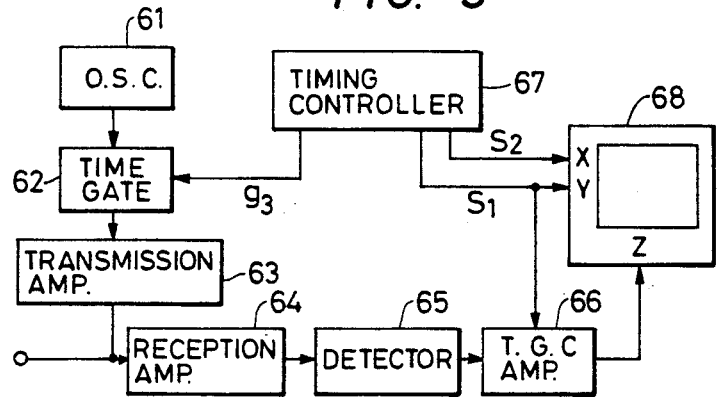
FIG. 3 is a block diagram of the details of the block 6 in FIG. 1.

FIG. 2 is a block diagram of the details of the pulse Doppler flow meter 2 in the embodiment of FIG. 1. An oscillator 22 is adapted to generate a sine wave of a predetermined frequency $f_o$ (2–10 MHz). A time gate 23 is adapted to be opened and closed by a gate pulse $g_1$ of a period of substantially around 200 μsec, which is synchronous with the phase of the oscillator 22, and pass therethrough an output wave from the oscillator 22. This passed waveform is amplified by a transmission amplifier 24 to thereby drive the ultrasonic probe 21. The echo generated by the transmission of such an ultrasonic wave is detected by the probe 21 and amplified by a reception amplifier 25. In a gate control circuit 26, the opening and closing of a time gate 27 is controlled by a gate pulse $g_2$, which is delayed by the turn-around time of a sonic wave between the probe 21 and the region of interest 1 with respect to the gate pulse $g_1$ applied to the time gate 23. Therefore, the reception signal passed through the time gate 27 turns into a reflection signal from the region of interest (the blood in a blood vessel in this embodiment). In the case where this blood is moved, the frequency of the reception signal causes a Doppler shift fd in accordance with the moving speed thereof. Such a reception signal of a frequency of fo+fd and oscillating signal of a frequency of fo are mixed in a mixer 28 and passed througyh a low-pass filter 29 to extract only a component of a frequency difference fd therebetween. This extracted component is inputted into a frequency/voltage converter 30 to obtain an output 31 which is representative of an actual flow rate proportional to fd.

As described above, the pulse Doppler flow meter 2 is adapted to designate a distance between the probe 21 and region of interest, and measure the Doppler shift of the frequency of an echo from the region of interest. The device used as the flow meter 2 is not limited to the circuit used in this embodiment; for example, the circuit disclosed in U.S. Pat. No. 3,953,823 may also be used.

The M-mode imaging apparatus 6 is adapted to image the actions of a reflecting body (for example, the wall of a blood vessel) in the vicinity of the region of interest. The opening and closing of a time gate 62 is controlled by a gate pulse $g_3$ from a timing controller 67, and the passage of an output wave from an oscillator through the gate 62 is allowed intermittently. A transmitting signal in a burst state thus obtained is amplified by a transmission amplifier 63 to thereby drive the probe 32. A reception signal obtained from the probe 32 is amplified by a reception amplifier 64 and detected by a detector 65. The detected signal is amplified by a time gain compensation amplifier 66, the gain of which is controlled by a saw-toothed signal $S_1$ which is synchronous with the pulse $g_3$. A signal in which the sonic wave attenuation difference due to the distance has been compensated by the amplifier 66 is applied as a Z-axis signal to be displayed, i.e. a brightness signal to a CRT display 68. The saw-toothed signal synchronous with the pulse $g_3$ is applied as a Y-axis scanning signal to the display 68. A saw-toothed signal $S_2$, the period of which is longer than the cardiac period of a region of interest, i.e. a signal $S_2$ of a period of, for example, around 2–4 sec is applied as an X-axis scanning signal to the display 68. Consequently, a two-dimensional image in which the Y- and X-axes represent the distance between the region of interest and probe 32 and the time, respectively, is obtained on the picture frame on the display 68.

Figure 6A:
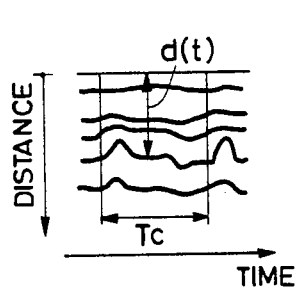
FIGS. 6A, 6B and 6C are schematic diagrams of the picture frame on the apparatus of FIG. 3.

FIG. 6A schematically illustrates an example of an M-mode image on the display 68 without the operation of the actuator 5, in which reference letters Tc denotes one period of cardiac motion. If the movement of the region of interest is designated by d(t) in the drawing, the distances between the probes 32, 21 and region of interest can be controlled to be constant by reproducing a waveform of d(t) by the synthesizer 7.

Figure 4:
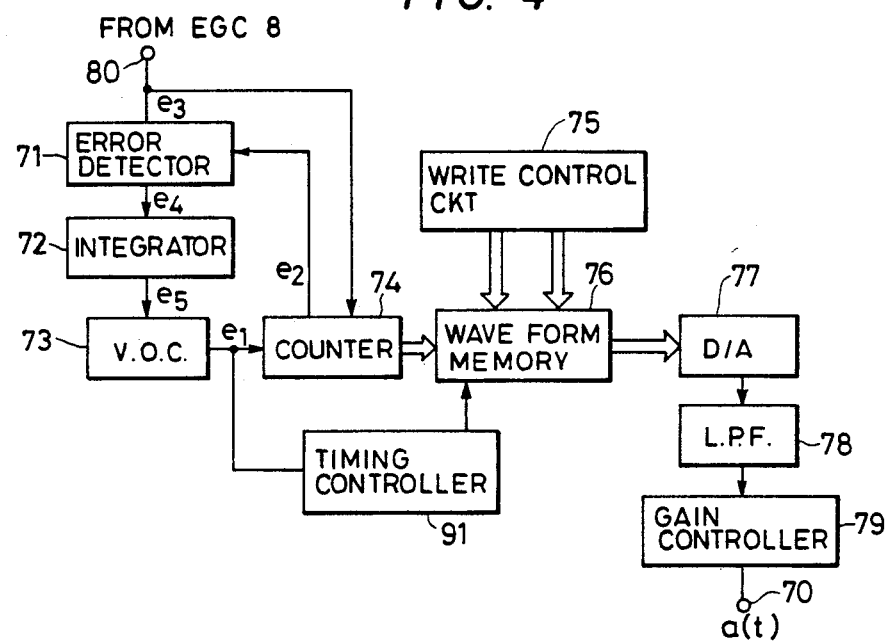
FIG. 4 is a block diagram of the details of the block 7 in FIG. 1.
Figure 5:
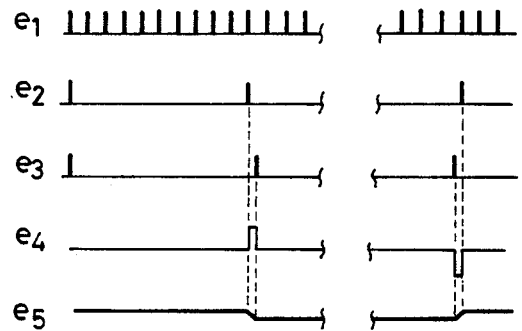
FIG. 5 is a time chart of an operation of the element the details of which are shown in FIG. 4.

FIG. 4 shows the detailed construction of the synthesizer 7. An output pulse train $e_1$ from a variable frequency oscillator 73 is inputted into a counter 74. When N pieces of pulses are inputted into the counter 74, an output signal $e_2$ is generated. A phase difference between the output signal and a pulse signal 80, which is obtained from the electrocardiograph 8, and which is synchronous with the cardiac motion of the living body is subjected to comparison in an error detector 71. An output $e_4$ from the error detector is a pulse signal having a polarity varying depending upon the order of two inputs, and a pulse width which is in accordance with the phase difference. This pulse signal $e_4$ is integrated in an integrator 72 to turn into a control voltage $e_5$ for the variable frequency oscillator. The elements 71, 72, 73, 74 form a phase locked loop, and a pulse signal 80, i.e. a pulse train, which is synchronous with the cardiac motion of the living body, and which has a frequency several times as many as that thereof, is obtained. FIG. 5 shows the waveforms $e_1$–$e_5$ of the signals and voltage generated in this section. The counter 74 is adapted to be reset by the pulse signal 80, and an output therefrom is used as a read address for a waveform memory 76.

Figure 6B:
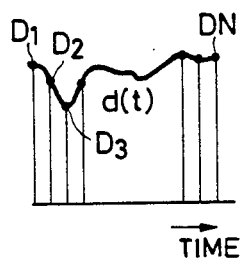

The addresses in the waveform memory 76 store therein parameters of displacement in various phases of a region of interest, i.e. the values shown at $D_1$, $D_2$, $D_3$ ... $D_N$ in FIG. 6B. A timing controller 91 generates a reading clock of the waveform memory 76 on the basis of an output from the variable frequency oscillator 73 as a reference clock. A read datum is converted into an analog signal by a D/A converter 77, and the resultant signal is shaped in a low-pass filter 78, this signal being then applied to a gain controller 79, from which a synthesizing output 70 is obtained. Accordingly, the waveform of the signal 70 becomes identical with the waveform stored in the waveform memory and reproduced synchronously with the heartbeat of the living body. The actuator 5 is driven by this signal 70, to thereby periodically move the probes 21, 32.

Figure 6C:
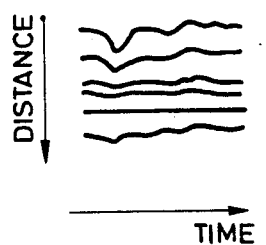

The above arrangement enables the distance between the probe 21, which is connected to the main measuring instrument, i.e. pulse Doppler flow meter 2, and the region of interest 1 to be controlled to a substantially constant level. FIG. 6C shows an example of a picture frame on the M-mode imaging apparatus 6 with the actuator 5 driven. When an image of the region of interest is substantially stopped on the M-mode image in the case where the actuator is operated, it proves that the waveform stored in the waveform memory 76 is suitable. When the waveform is not suitable, the content of the waveform memory 76 is corrected by using the write control circuit 75, or the amplitude of the output 70 is adjusted by the gain controller 79.

If a two-dimensional input tablet is laminated on the display frame on the CRT display in the M-mode imaging apparatus 6 as a means for inputting a waveform into the waveform memory 76, the setting of a suitable waveform can be done easily.

Figure 7:
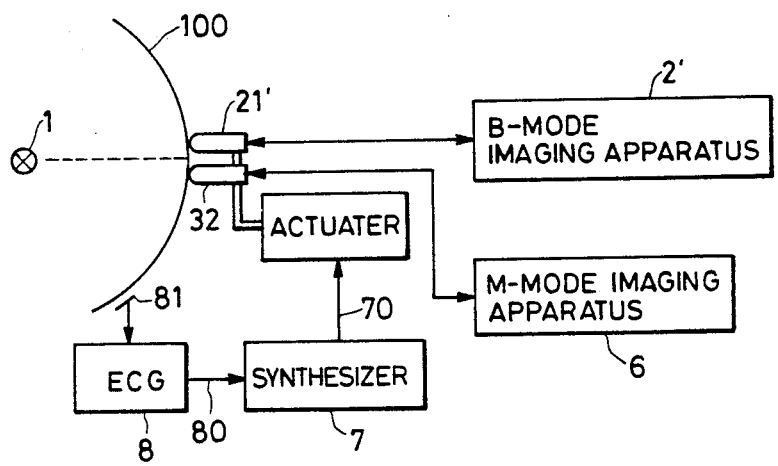
FIG. 7 is a block diagram of another embodiment.

Besides the Doppler flow meter, a B-mode imaging apparatus can also be used as the main measuring instrument. An embodiment using a B-mode imaging apparatus is as shown in FIG. 7. In this embodiment, an array type ultrasonic probe 21' instead of the probe 21 shown in FIG. 1 is mounted with a movement detecting probe 32 on an actuator 5, and these probes are driven by an output from a synthesizer 7. The probe 21' is connected to the B-mode imaging apparatus 2'. In the B-mode imaging apparatus, the imaging of a tomogram based on the known electronic sector scanning or electronic linear scanning is done by using the probe 21'. The construction of the remaining portions of this embodiment is identical with that of the corresponding portions of the embodiment of FIGS. 1–6. According to the structure of the embodiment of FIG. 7, high definition tomographic images of a region of interest 1 can be obtained irrespective of the movement thereof due to the cardiac motion thereof.

What is claimed is:

1. An ultrasonic measurement apparatus comprising a main measuring instrument means for applying transmit signals, a first ultrasonic probe means responsive to said main measuring instrument means for transmitting and receiving ultrasonic waves to and from a region of interest in a living body and supplying signals representative thereof to said main measuring instrument means, a second ultrasonic probe means provided in the vicinity of said first probe and adapted to detect the movement of a reflecting body local to said region of interest in the interior of said living body, and moving due to cardiac motion an M-mode imaging apparatus adapted to apply a transmitting wave signal repeatedly with a time of repetition to said second ultrasonic probe means, and to display a reception signal from said second ultrasonic probe means on a two-dimensional image as the detected movement, one axis thereof being representative of a distance between said second ultrasonic probe means and the region of interest and the other axis thereof being the lapse of said time of repetition, means for detecting a signal representative of periodic cardiac motion in said living body and for generating a pulse signal which is synchronous therewith, synthesizer means for generating a set waveform output synchronously with said pulse signal, and actuator means responsive to said output from said synthesizer means for periodically moving said first and second ultrasonic probe means so as to maintain variations in relative distance between said first and second ultrasonic probe means and said region of interest and reflecting body local thereto within a predetermined range of distance thereby to compensate for the effect of motion of said region of interest due to cardiac motion on said main measurement instrument means.

2. An ultrasonic measurement apparatus according to claim 1, wherein said main measuring instrument means comprises a Doppler flow meter.

3. An ultrasonic measurement apparatus according to claim 1, wherein said main measuring instrument means comprises a B-mode imaging apparatus.

4. An ultrasonic measurement apparatus according to claim 1, wherein said cardiac motion detecting means comprises an electrocardiographic detecting means adapted to obtain an ECG signal from said living body.

5. An ultrasonic measurement apparatus according to claim 1, wherein said synthesizer means includes a phase locked loop circuit adapted to generate a pulse train, which is synchronous with said pulse signal, and which has a frequency several times as many as that thereof, a waveform memory adapted to store a waveform of movement of said reflecting body local to said region of interest, and to be read periodically by said pulse train.

* * * * *